United States Patent [19]

Delony et al.

[11] 4,021,324

[45] May 3, 1977

[54] METHOD FOR ELECTROPHORETIC DESTAINING

[75] Inventors: Timothy Edwin Delony, Oakland; James R. Gangwer, Alameda; James F. Monthony, Albany, all of Calif.

[73] Assignee: Bio-Rad Laboratories, Inc., Richmond, Calif.

[22] Filed: Sept. 8, 1975

[21] Appl. No.: 610,941

[52] U.S. Cl. .................. 204/180 G; 204/180 B; 204/180 R; 204/299 R
[51] Int. Cl.[2] .................. G01N 27/26; G01N 27/30
[58] Field of Search .......... 204/180 R, 130, 180 B, 204/180 G, 299, 283, 301

[56] References Cited

UNITED STATES PATENTS

| | | | |
|---|---|---|---|
| 2,788,319 | 4/1957 | Pearson | 204/180 B X |
| 3,244,612 | 4/1966 | Murphy | 204/294 |
| 3,444,062 | 5/1969 | Felici et al. | 204/301 X |
| 3,544,458 | 12/1970 | Sato | 210/65 |
| 3,682,806 | 8/1972 | Kinsella et al. | 204/180 B X |

*Primary Examiner*—Arthur C. Prescott
*Attorney, Agent, or Firm*—Townsend and Townsend

[57] ABSTRACT

Electrophoretic gels are destained between two layers of ion exchange resin. Electrical current is passed from one layer of resin to the other through the gel in an electrically low-conductive surrounding medium such as de-ionized water. Virtually all of the current goes through the gel resulting in the highly efficient destaining technique.

4 Claims, 1 Drawing Figure

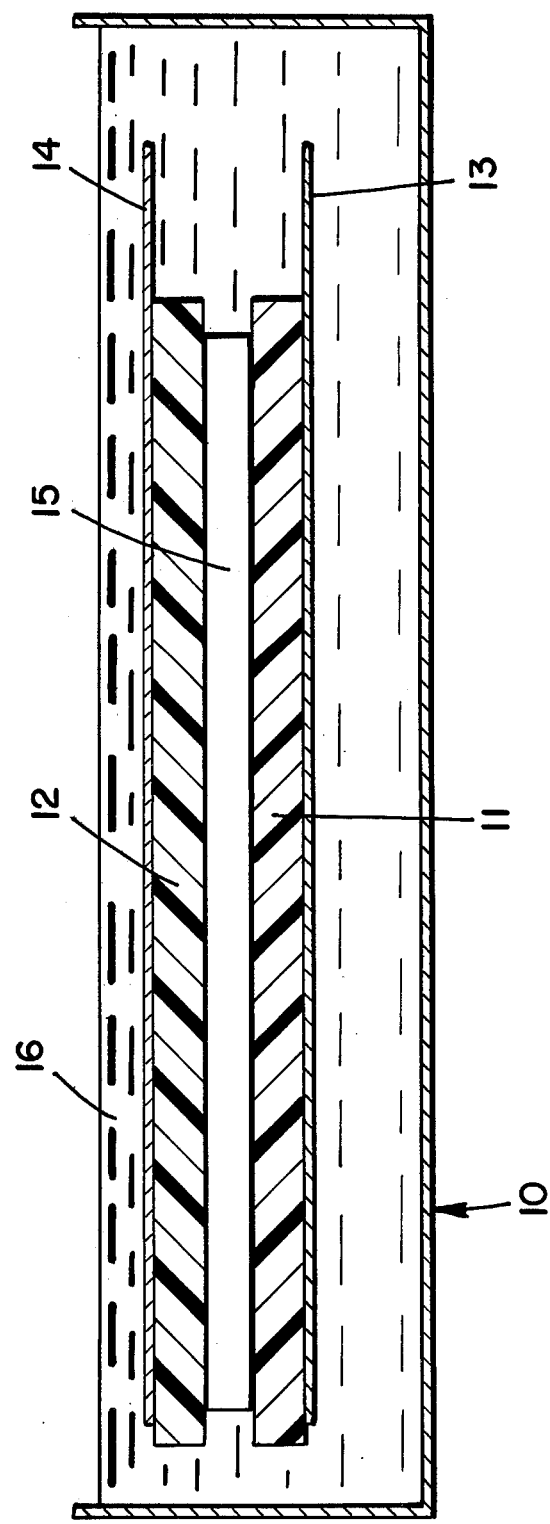

METHOD FOR ELECTROPHORETIC DESTAINING

This invention relates to gel electrophoresis. More particularly it relates to that procedure commonly practiced in gel electrophoresis known as destaining by electrophoretic removal of excess and unbound stain from the gel.

In most of the devices in current use for the electrophoretic destaining of gels such as polyacrylamide gel rods, the gels are supported between two reservoirs of a conductive solution (normally dilute acetic acid). When a dc voltage is applied to electrodes in each reservoir, current flows through the solution and the gels, moving the stain into one of the reservoirs depending upon the direction of current flow. This family of destainers is comprised of two major sub-units: First, those in which the current is applied through the gel longitudinally (see: Davis, B. J., *Ann. N.Y. Acad. Sci.* 121, Art 2, 407 [1964]). Second, those in which the current is applied across the diameter of the gel (see: Schwabe, C.,*Anal. Biochem.* 17, 201–209 [1966]; Peterson, J., *Anal. Biochem.* 25, 257–259 [1970]; Ward S., *Anal. Biochem.* 33, 259–262 [1970]; and Farmer, R., Turano, P., and Turner, W., *J. Chromatogr.* 24, 204–205 [1966]). The latter type is obviously more efficient, since the current has a shorter path.

The great drawback in using these bath type destainers is the inability of the user to form a tight seal between the gels and each of the two reservoirs. This problem increases the destaining time since the current prefers to go through the leak rather than through the gel.

Attempts have been made by researchers to make a "dry" type destainer, i.e., one in which the current has no other path except through the gel. (See: Datyner, A., and Finnimore, E., *Anal. Biochem.* 52, 45–55 [1973]; and Shortess, D., *Anal. Biochem.* 60, 329–331 [1974]). However, these instruments are either very expensive (Datyner & Finnimore) or still require acetic acid as a current carrier (Shortness).

In accordance with the present invention a method for destaining an electrophoretic gel is provided which comprises disposing the gel to be destained between two beds of ion exchange resin, and applying an electrical potential across said resin beds to cause sufficient current to flow from one of said resin beds to the other through said gel to move unbound stain out of said gel and onto one of said resin beds. In the preferred embodiment each resin bed is formed from a mixture of strong anion exchange resin and strong cation exchange resin. The advantage of using such a mixture instead of either an anion exchange resin or a cation exchange resin alone is that the stain moved out of the gel is bound firmly by the receiving resin. The removed stain can not contaminate other portions of the apparatus or fluids employed in the destaining operation.

Generally, the ion exchange resin will be of the styrene-divinyl benzene copolymer family. A useful ion exchange resin of this type is an anion resin in the acetate form. Since most destaining is performed in the presence of some acetic acid, the use of such a resin is fully compatible with the ionic content of the commonly used fluids. Where the anion/cation combination bed is utilized, the cation exchange resin may suitably be in sulfonic acid form.

In practicing the present method, suitable apparatus may include those parts and materials shown schematically in the accompanying drawing. Thus, a fluid holding tank 10 may have mounted therein a pair of spaced apart parallel generally flat layers of ion exchange resin 11 and 12. The ion exchange resin layers 11 and 12 may typically be formed from a combination of equal parts of strong cation and strong anion resins such as those commercially available from Bio-Rad Laboratories, Richmond, Calif., and known as AG 1–X8 acetate form and AG 50W–X8 which has sulfonic acid exchange groups in their protio form and quatenary amine exchange groups in their acetate form. Resin layer 11 includes electrode 13 attached thereto, while resin layer 12 has electrode 14 similarly attached. The resin layers 11 and 12 are suitably mounted within tank 10 so as to avoid electrical contact therewith. Tank 10 may, therefore, be either made from electrically nonconductive material or resin layers 11 and 12 can be supported therein on suitable insulative material.

Resin layers 11 and 12 are mounted in substantially spaced apart parallel relationship with the space therebetween adapted for receiving a gel sample 15 for destaining. Gel sample 15 may typically be in either a rod or slab configuration. Gel sample 15 is in electrical communication with each of the mutually facing surfaces of resin layers 11 and 12. Electrodes 13 and 14 are attached to the non-mutually facing surfaces (resin layers surfaces which are opposite from and out of contact with the gel) of resin layers 11 and 12 respectively. Current flows through the resin layers to reach the electrodes.

In a preferred embodiment, tank 10 is filled with an electrically low-conductive fluid such as de-ionized water 16. The liquid is included primarily as a heat sink.

Since both the resin layers and the gel are more conductive than the surrounding fluid such as the de-ionized water, a preferential path from one resin layer through the gel to the opposed resin layer is created which is conductive to gel destaining. The present relationship is more advantageous than the prior art which utilized conductive liquids to carry current to the gel since there is no leakage or alternative path for current. Substantially all of the current passes through the gel in the present invention resulting in a faster destaining operation.

Aside from the use of ion exchange resin to carry current to and from the gel to be destained, the present invention is in other ways equivalent to prior art methods used for electrophoretic destaining. Thus, other process details such as the current and voltages previously used are applicable.

We claim:

1. A method for destaining an electrophoretic gel comprising: disposing the gel to be destained between two beds of ion exchange resin, and applying an electrical potential across said resin beds to cause sufficient current to flow from one of said resin beds through said gel to move unbound stain out of said gel, and into the other resin bed.

2. A method for destaining in accordance with claim 1, wherein each of said resin beds is formed from a mixture of strong cation and anion exchange resins.

3. A method for destaining in accordance with claim 1, wherein each of said ion exchange resin beds is formed from a mixture of styrene-divinyl benzene copolymer having sulfonic acid exchange groups in their protio form and quatenary amine exchange groups in their acetate form.

4. A method for destaining in accordance with claim 1, wherein said gel to be destained is a polyacrylamide gel in rod or slab form, and each of said two beds of resin is in contact with opposite sides of the gel.

* * * * *